(12) United States Patent
Audousset

(10) Patent No.: US 7,141,079 B2
(45) Date of Patent: Nov. 28, 2006

(54) OXIDATION DYEING COMPOSITION FOR KERATINOUS FIBERS AND DYEING METHOD USING SAME

(75) Inventor: Marie-Pascale Audousset, Asniéres (FR)

(73) Assignee: L'Oreal (FR)

( * ) Notice: Subject to any disclaimer, the term of this patent is extended or adjusted under 35 U.S.C. 154(b) by 0 days.

(21) Appl. No.: 10/257,358

(22) PCT Filed: Apr. 11, 2001

(86) PCT No.: PCT/FR01/01109

§ 371 (c)(1), (2), (4) Date: Nov. 27, 2002

(87) PCT Pub. No.: WO01/78667

PCT Pub. Date: Oct. 25, 2001

(65) Prior Publication Data

US 2004/0010862 A1 Jan. 22, 2004

(30) Foreign Application Priority Data

Apr. 12, 2000 (FR) .................................. 00 04719

(51) Int. Cl.
*A61K 7/13* (2006.01)

(52) U.S. Cl. .................. 8/405; 8/406; 8/408; 8/409; 8/410; 8/411; 8/412; 8/421; 8/568; 546/249

(58) Field of Classification Search .............. 8/405, 8/406, 408, 409, 410, 411, 412, 414, 421, 8/568; 546/249

See application file for complete search history.

(56) References Cited

U.S. PATENT DOCUMENTS

| | | |
|---|---|---|
| 2,798,053 A | 7/1957 | Brown |
| 3,836,537 A | 9/1974 | Boerwinkle et al. |
| 3,879,376 A | 4/1975 | Vanlerberghe et al. |
| 3,915,921 A | 10/1975 | Schlatzer, Jr. |
| 3,953,608 A | 4/1976 | Vanlerberghe et al. |
| 4,003,699 A | 1/1977 | Rose et al. .................. 8/10.2 |
| 4,031,025 A | 6/1977 | Vanlerberghe et al. |
| 4,157,388 A | 6/1979 | Christiansen |
| 4,185,087 A | 1/1980 | Morlino |
| 4,217,914 A | 8/1980 | Jacquet et al. |
| 4,237,243 A | 12/1980 | Quack et al. |
| 4,390,689 A | 6/1983 | Jacquet et al. |
| 4,422,853 A | 12/1983 | Jacquet et al. |
| 4,473,375 A * | 9/1984 | Clausen .................. 8/409 |
| 4,509,949 A | 4/1985 | Huang et al. |
| 4,702,906 A | 10/1987 | Jacquet et al. |
| 4,719,282 A | 1/1988 | Nadolsky et al. |
| 4,754,069 A | 6/1988 | Braun et al. ............... 564/440 |
| 4,823,985 A | 4/1989 | Grollier et al. ............. 322/1 |
| 4,904,275 A | 2/1990 | Grollier |
| 4,948,579 A | 8/1990 | Jacquet et al. |
| 5,061,289 A | 10/1991 | Clausen et al. ............. 8/405 |
| 5,196,189 A | 3/1993 | Jacquet et al. |
| 5,380,340 A | 1/1995 | Neunhoeffer et al. ........ 8/409 |
| 5,645,610 A | 7/1997 | Balzer et al. ............... 8/411 |
| 5,766,576 A | 6/1998 | Lowe et al. ................ 424/62 |
| 5,919,273 A | 7/1999 | Rondeau et al. |
| 5,976,195 A * | 11/1999 | de la Mettrie et al. ....... 8/411 |
| 5,993,490 A | 11/1999 | Rondeau et al. |
| 6,099,592 A | 8/2000 | Vidal et al. ................ 8/409 |
| 6,099,593 A | 8/2000 | Terranova et al. |
| 6,342,078 B1 | 1/2002 | De La Mettrie et al. |

FOREIGN PATENT DOCUMENTS

| | | |
|---|---|---|
| DE | 23 59 399 | 6/1975 |
| DE | 31 32 885 | 3/1983 |
| DE | 38 43 892 | 6/1990 |
| DE | 41 33 957 | 4/1993 |
| DE | 195 43 988 | 5/1997 |
| DE | 195 45 854 | 6/1997 |
| DE | 196 10 946 | 9/1997 |
| DE | 198 28 204 | 10/1999 |
| EP | 0 095 238 | 11/1983 |
| EP | 0 166 155 | 1/1986 |
| EP | 0 173 109 | 3/1986 |
| EP | 0 216 479 | 4/1987 |
| EP | 122 324 | 1/1988 |
| EP | 503 853 | 9/1992 |
| EP | 0 530 974 | 7/1995 |
| EP | 0 687 669 | 12/1995 |
| EP | 0 687 669 A1 | 12/1995 |
| EP | 0 791 352 B1 | 8/1997 |
| EP | 0 815 885 | 1/1998 |

(Continued)

OTHER PUBLICATIONS

Co-pending Application No., Composition for the Oxidation Dyeing of Keratin Fibres, Comprising A 3,5-Diamino-pyridine Derivative and a Particular Thickening Polymer, Marie-Pascale Audousset, filed Oct. 11, 2002.

(Continued)

*Primary Examiner*—Eisa Elhilo
(74) *Attorney, Agent, or Firm*—Finnegan, Henderson, Farabow, Garrett and Dunner, L.L.P.

(57) ABSTRACT

The invention concerns an oxidation dyeing composition for keratinous fibers, and in particular human keratinous fibers such as hair comprising, in a medium suited for dyeing: as first coupling agent at least a 3,5-diaminopyridine derivative suitably selected; and as second coupling agent at least a meta-phenylenediamine, and/or one of its addition salts with an acid; and at least an oxidation base such as para-phenylenediamine and/or one of its addition salts with an acid. The invention also concerns the dyeing method using said composition.

29 Claims, No Drawings

FOREIGN PATENT DOCUMENTS

| | | |
|---|---|---|
| FR | 2 137 684 | 12/1972 |
| FR | 2 270 846 | 12/1975 |
| FR | 2 416 723 | 9/1979 |
| FR | 2 586 913 | 3/1987 |
| FR | 2 633 940 | 1/1990 |
| FR | 2 733 749 | 11/1996 |
| FR | 2 750 048 | 12/1997 |
| GB | 1 026 978 | 4/1966 |
| GB | 1 153 196 | 5/1969 |
| JP | 58-34857 A | 3/1983 |
| JP | 61-152620 A | 7/1986 |
| JP | 2-19576 | 1/1990 |
| JP | 20-19576 | 1/1990 |
| JP | 5-186319 A | 7/1993 |
| JP | 7-309732 A | 11/1995 |
| JP | 8-3121 A | 1/1996 |
| JP | 9-110659 | 4/1997 |
| JP | 10-218746 A | 8/1998 |
| JP | 2000-86471 A | 3/2000 |
| WO | WO 94/08969 | 4/1994 |
| WO | WO 94/08970 | 4/1994 |
| WO | WO 96/15765 | 5/1996 |
| WO | WO 99/17733 A1 | 4/1999 |

OTHER PUBLICATIONS

Co-pending U.S. Appl. No. 10/257,418, Composition for the Oxidation Dyeing of Keratin Fibers, Comprising a 3,5-Diaminopyridine Derivative and a Cationic or Amphoteric Polymer, Marie-Pascale Audousset, filed Oct. 11, 2002.

Co-pending U.S. Appl. No. 10/257,355, Oxidation Dyeing Composition for Keratinous Fibres and Method Using Same, Marie-Pascale Audousset, filed Oct. 11, 2002.

Co-pending U.S. Appl. No. 10/257,356, Oxidation Dyeing Composition for Keratinous Fibres and Method Using Same, Marie-Pascale Audousset, filed Oct. 11, 2002.

English language Derwent Abstract of DE 195 45 854, Jun. 12, 1997.

English language Derwent Abstract of DE 196 10 946, Sep. 25, 1997.

English language Derwent Abstract of De 198 28 204, Oct. 28, 1999.

English language Derwent Abstract of JP2-19576, Jan. 23, 1990.

English language Derwent Abstract of JP 9-110659, Apr. 28, 1997.

English language Derwent Abstract of EP 0 791 352, Aug. 27, 1997.

English language Abstract for FR 2 633 940.

English language Patent Abstracts of Japan for JP 5-186319 A.

English language Patent Abstracts of Japan for JP 7-309732 A.

English language Patent Abstracts of Japan for JP 2000-86471 A.

English language Derwent Abstract of JP 20-19576.

Office Action in co-pending U.S. Appl. No. 10/257,355, dated Jan. 12, 2005 (Ex. Elhilo).

Office Action in co-pending U.S. Appl. No. 10/257,356, dated Feb. 1, 2005 (Ex. Elhilo).

Office Action in co-pending U.S. Appl. No. 10/257,418, dated Jul. 14, 2004 (Ex. Elhilo).

Office Action in co-pending U.S. Appl. No. 10/398,423, dated May 12, 2005 (Ex. Elhilo).

* cited by examiner

OXIDATION DYEING COMPOSITION FOR KERATINOUS FIBERS AND DYEING METHOD USING SAME

The invention relates to a composition for the oxidation dyeing of keratinous fibers, and in particular of human keratinous fibers such as the hair, comprising, in a medium which is suitable for dyeing,
as a first coupler, at least one suitably chosen 3,5-diaminopyridine derivative;
and, as a second coupler, at least one meta-phenylenediamine and/or one of its addition salts with an acid;
and at least one oxidation base of the para-phenylenediamine type and/or one of its addition salts with an acid.

The invention also relates to the dyeing method using this composition.

It is known practice to dye keratinous fibers, and in particular human hair, with dye compositions containing oxidation dye precursors, in particular ortho- or para-phenylenediamines, ortho- or para-aminophenols and heterocyclic bases which are generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being chosen in particular from aromatic meta-diamines, meta-aminophenols, meta-diphenols and certain heterocyclic compounds.

The variety of molecules used as regards the oxidation bases and the couplers allows a wide range of colors to be obtained.

The "permanent" coloration obtained by means of these oxidation dyes must, moreover, satisfy a certain number of requirements. Thus, it must be able to give shades of the desired intensity and it must be able to withstand external agents (light, bad weather, washing, permanent-waving, perspiration, rubbing).

The dyes must also make it possible to cover white hair and, finally, they must be as unselective as possible, i.e. they must give the smallest possible color differences along the same length of keratinous fiber, which may in fact be differently sensitized (i.e. damaged) between its tip and its root.

Oxidation dyeing compositions containing certain 3,5-diaminopyridine derivatives as coupler, in combination with oxidation bases conventionally used in oxidation dyeing, such as, for example, para-phenylenediamines or para-aminophenols, have already been proposed, in particular in patents U.S. Pat. No. 4,473,375 and DE 31 32 885. Such compositions are not, however, always satisfactory, in particular from the point of view of the strengths and the chromaticity of the colorations obtained.

The applicant has now just discovered, completely unexpectedly and surprisingly, that it is possible to obtain novel dyes that are capable of giving strong, particularly chromatic and brilliant, relatively unselective colorations which show excellent properties of resistance to the various attacking factors to which the keratinous fibers may be subjected, by combining a 3,5-diaminopyridine derivative of formula (I) defined below with a second coupler of the meta-phenylenediamine type and with an oxidation base of the para-phenylenediamine type.

These discoveries form the basis of the present invention.

A first subject of the invention is therefore a composition for the oxidation dyeing of keratinous fibers, and in particular of human keratinous fibers such as the hair, characterized in that it comprises, in a medium which is suitable for dyeing:
as a first coupler, at least one 3,5-diaminopyridine derivative corresponding to the following general formula (I):

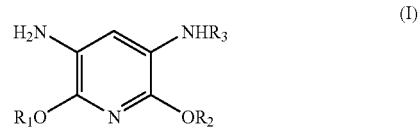

in which:
$R_1$ and $R_2$, which may be identical or different, represent a $C_1$–$C_4$ alkyl radical, a $C_1$–$C_4$ monohydroxyalkyl radical or a $C_2$–$C_4$-polyhydroxyalkyl radical,
$R_3$ represents a hydrogen atom, a $C_1$–$C_4$ alkyl radical, a $C_1$–$C_4$ monohydroxyalkyl radical or a $C_2$–$C_4$ polyhydroxyalkyl radical and/or one of its addition salts with an acid;
and, as a second coupler, a meta-phenylenediamine and/or one of its addition salts with an acid;
at least one oxidation base of the para-phenylenediamine type and/or one of their addition salts with an acid.

The dye composition in accordance with the invention gives strong, very chromatic colorations which show excellent properties of withstanding not only atmospheric agents such as light and bad weather, but also perspiration and the various treatments to which the hair may be subjected.

A subject of the invention is also a method for the oxidation dyeing of keratinous fibers using this dye composition.

Among the 3,5-diaminopyridine derivatives of formula (I) in accordance with the invention, mention may be made of 2,6-dimethoxy-3,5-diaminopyridine, 2,6-diethoxy-3,5-diaminopyridine, 2,6-di-(β-hydroxyethyloxy)-3,5-diaminopyridine and their addition salts with an acid.

According to the invention, the dye composition preferably contains 2,6-dimethoxy-3,5-diaminopyridine and/or at least one of its addition salts with an acid.

The 3,5-diaminopyridine derivative(s) of formula (I) which can be used as a first coupler in the dye composition in accordance with the invention preferably represent(s) from 0.0001 to 10% by weight approximately of the total weight of the dye composition, and even more preferentially from 0.005 to 5% by weight approximately of this weight.

Among the meta-phenylenediamine(s) which can be used as a second coupler in the dye compositions in accordance with the invention, mention may in particular be made of the following compounds of formula (II) and their addition salts with an acid:

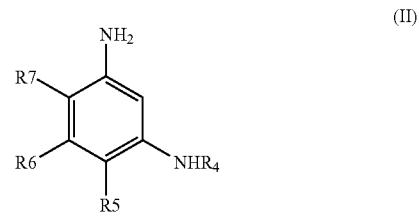

in which:

$R_4$ represents a hydrogen atom, a $C_1$–$C_4$ alkyl radical, a $C_1$–$C_4$ monohydroxyalkyl radical or a $C_2$–$C_4$ polyhydroxyalkyl radical;

$R_5$ and $R_6$, which may be identical or different, represent a hydrogen atom, a $C_1$–$C_4$ alkyl radical or a $C_1$–$C_4$ hydroxyalkoxy radical;

$R_7$ represents a hydrogen atom, a $C_1$–$C_4$ alkoxy radical, a $C_1$–$C_4$ aminoalkoxy radical, a $C_1$–$C_4$ monohydroxyalkoxy radical, a $C_2$–$C_4$ polyhydroxyalkoxy radical or a 2,4-diaminophenoxyalkoxy radical.

Among the meta-phenylenediamines of formula (II) above, mention may more particularly be made of meta-phenylenediamine, 2,4-diaminophenoxyethanol, 2,4-diamino-1-ethoxybenzene, 2-amino-4-N-(β-hydroxyethyl)aminoanisole, 3,5-diamino-1-ethyl-2-methoxybenzene, 3,5-diamino-2-methoxy-1-methylbenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxyproploxy)benzene and 2-amino-4-N-(β-hydroxyethyl)amino-1-methoxybenzene, and their addition salts with an acid.

The meta-phenylenediamine(s) in accordance with the invention preferably represent(s) from 0.0001 to 10% by weight approximately of the total weight of the dye composition, and even more preferentially from 0.005 to 5% by weight approximately of this weight.

Among the para-phenylenediamines which can be used as an oxidation base in the dye compositions in accordance with the invention, mention may in particular be made of the following compounds of formula (III) and their addition salts with an acid:

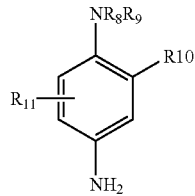

(III)

in which:

$R_8$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous, phenyl or 4'-aminophenyl group;

$R_9$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;

$R_{10}$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino$(C_1$–$C_4)$alkoxy radical, a $C_1$–$C_4$ mesylaminoalkoxy radical or a carbamoylamino$(C_1$–$C_4)$alkoxy radical, $R_{11}$ represents a hydrogen or halogen atom or a $C_1$–$C_4$ alkyl radical.

Among the nitrogenous groups of formula (III) above, mention may in particular be made of amino, mono$(C_1$–$C_4)$alkylamino, di$(C_1$–$C_4)$alkylamino, tri$(C_1$–$C_4)$alkylamino, monohydroxy$(C_1$–$C_4)$alkylamino, imidazolinium and ammonium radicals.

Among the para-phenylenediamines of formula (III) above, mention may more particularly be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-paraphenylenediamine and 2-methyl-1-N-(β-hydroxyethyl)-para-phenylenediamine, and their addition salts with an acid.

Among the para-phenylenediamines of formula (III) above, para-phenylenediamine, para-tolylenediamine, 2-isopropyl-para-phenylenediamine, 2-β-hydroxyethyl-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and their addition salts with an acid, are most particularly preferred.

The para-phenylenediamines preferably represent from 0.0005 to 12% by weight approximately of the total weight of the dye composition in accordance with the invention, and even more preferentially from 0.005 to 6% by weight approximately of this weight.

The dye composition in accordance with the invention may also contain, in addition to the compound(s) of formula (I) above and to the meta-phenylenediamine(s), one or more additional couplers which may be chosen from the couplers conventionally used in oxidation dyeing, and among which mention may in particular be made of meta-aminophenols, meta-diphenols and heterocyclic couplers such as, for example, indole derivatives, indoline derivatives, pyridine derivatives other than those of the invention and pyrazolones, and their addition salts with an acid.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methyl benzene, 4-chloro-1,3-dihydroxybenzene, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one and 3-(4-hydroxy-1-methyl-1H-indol-5-ylmethyl)-1-methylpyridinium, and their addition salts with an acid.

When they are present, these additional couplers preferably represent from 0.0001 to 10% by weight approximately of the total weight of the dye composition, and even more preferentially from 0.005 to 5% by weight approximately of this weight.

In addition to the para-phenylenediamines used as oxidation bases, the oxidation dyeing composition in accordance with the invention may contain one or more additional oxidation bases which are preferably chosen from the oxidation bases conventionally used in oxidation dyeing, and among which mention may in particular be made of bisphenylalkylenediamines, para-aminophenols, ortho-aminophenols and heterocyclic bases.

Among the bisphenylalkylenediamines, mention may more particularly be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and their addition salts with an acid.

Among the para-aminophenols, mention may more particularly be made, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and their addition salts with an acid.

Among the ortho-aminophenols, mention may more particularly be made, by way of example, of 2-aminophenol, 2-amino-5-methylphenol, 2-amino-6-methylphenol and 5-acetamido-2-aminophenol, and their addition salts with an acid.

Among the heterocyclic bases, mention may more particularly be made, by way of example, of pyridine derivatives, pyrimidine derivatives and pyrazole derivatives.

Among the pyridine derivatives, mention may more particularly be made of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and their addition salts with an acid.

Among the pyrimidine derivatives, mention may more particularly be made of the compounds described, for example, in German patent DE 2 359 399 or Japanese patent JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine.

Among the pyrazole derivatives, mention may more particularly be made of the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole and 4,5-diamino-1-β-hydroxyethylpyrazole, and their addition salts with an acid.

The additional oxidation base(s) preferably represent(s) from 0.0005 to 12% by weight approximately of the total weight of the dye composition, and even more preferentially from 0.005 to 6% by weight approximately of this weight.

In general, the addition salts with an acid which can be used in the context of the dye compositions of the invention (pyrazolopyrimidines, compounds of formula (I), additional couplers and oxidation bases) are in particular chosen from hydrochlorides, hydrobromides, sulfates, citrates, succinates, tartrates, lactates and acetates.

The medium which is suitable for dyeing (or support) generally consists of water or of a mixture of water and at least one organic solvent in order to solubilize the compounds which would not be sufficiently water-soluble. By way of organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents may be present in proportions preferably of between 1 and 40% by weight approximately relative to the total weight of the dye composition, and even more preferentially between 5 and 30% by weight approximately.

The pH of the dye composition in accordance with the invention is generally between 3 and 12 approximately, and preferably between 5 and 11 approximately. It may be adjusted to the desired value by means of acidifying or basifying agents usually used in the dyeing of keratinous fibers.

Among the acidifying agents, mention may be made, by way of example, of inorganic or organic acids such as hydrochloric acid, orthophosphoric acid, sulfuric acid, carboxylic acids such as acetic acid, tartaric acid, citric acid or lactic acid, and sulfonic acids.

Among the basifying agents, mention may be made, by way of example, of aqueous ammonia, alkaline carbonates, alkanolamines such as mono-, di- and triethanolamines, and derivatives thereof, sodium hydroxide, potassium hydroxide and the compounds of formula (IV) below:

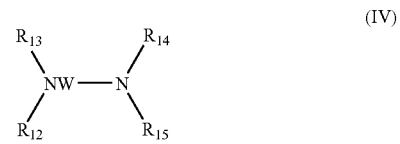

(IV)

in which W is a propylene residue optionally substituted with a hydroxyl group or a $C_1$–$C_6$ alkyl radical; $R_{12}$, $R_{13}$, $R_{14}$ and $R_{15}$, which may be identical or different, represent a hydrogen atom, a $C_1$–$C_6$ alkyl radical or a $C_1$–$C_6$ hydroxyalkyl radical.

The oxidation dyeing compositions in accordance with the invention may also contain at least one direct dye, in particular to modify the shades or enrich them with glints.

The dye composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestering agents, fragrances, buffers, dispersing agents, conditioners, such as, for example, volatile or nonvolatile silicones, which are modified or unmodified, film-forming agents, ceramides, preserving agents and opacifiers.

Of course, those skilled in the art will take care to choose this or these optional additional compound(s) such that the advantageous properties intrinsically associated with the oxidation dyeing composition in accordance with the invention are not, or are not substantially, adversely affected by the addition(s) envisioned.

The dye composition according to the invention may be in various forms, such as in the form of liquids, of creams or of gels, or in any other form which is suitable for dyeing keratinous fibers, and in particular human hair.

Another subject of the invention is a method for the oxidation dyeing of keratinous fibers, and in particular human keratinous fibers such as the hair, using the dye composition as defined above.

According to this method, at least one dye composition as defined above is applied to the fibers, the color being developed at acidic, neutral or alkaline pH using an oxidizing agent which is added to the dye composition just at the time of use, or which is present in an oxidizing composition applied simultaneously or sequentially.

According to a preferred embodiment of the dyeing method of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratinous fibers and is left to stand on them for approximately 3 to 50 minutes, preferably approximately 5 to 30 minutes, after which the fibers are rinsed, washed with shampoo, rinsed again and dried.

The oxidizing agent may be chosen from the oxidizing agents conventionally used for the oxidation dyeing of keratinous fibers, and among which mention may be made of hydrogen peroxide, urea peroxide, alkali metal bromates, persalts such as perborates and persulfates, and enzymes such as peroxidases, laccases, tyrosynases and oxidoreductases, among which mention may in particular be made of pyranose oxidases, glucose oxidases, glycerol oxidases, lactate oxidases, pyruvate oxidases and uricases.

The pH of the oxidizing composition containing the oxidizing agent as defined above is such that, after mixing it with the dye composition, the pH of the resulting composition applied to the keratinous fibers preferably ranges between approximately 3 and 12, and even more preferentially between 5 and 11. It is adjusted to the desired value by means of acidifying or basifying agents usually used in the dyeing of keratinous fibers and as defined above.

The oxidizing composition as defined above may also contain various adjuvants conventionally used in compositions for dyeing the hair and as defined above.

The composition which is finally applied to the keratinous fibers may be in various forms, such as in the form of liquids, of creams or of gels, or in any other form which is suitable for dyeing keratinous fibers, and in particular human hair.

Finally, a subject of the invention is a multicompartment device or dyeing "kit" or any other multicompartment packaging system, a first compartment of which contains the dye composition as defined above and a second compartment of which contains the oxidizing composition as defined above. These devices may be equipped with a means for applying the desired mixture to the hair, such as the devices described in patent FR-2 586 913 in the name of the applicant.

The examples which follow are intended to illustrate the invention without, however, limiting the scope thereof.

| DYEING EXAMPLES | 1 | 2 | 3 |
|---|---|---|---|
| 2,6-Dimethoxy-3,5-diaminopyridine dihydrochloride (coupler of formula (I) ) | 0.726 | 0.361 | 0.484 |
| 2,4-Diaminophenoxyethanol dihydrochloride (meta-phenylenediamine) | 0.241 | — | 0.241 |
| 2-Amino-4-N-(β-hydroxyethyl) aminoanisole dihydrochloride (meta-phenylenediamine) | — | 0.255 | — |
| Para-phenylenediamine (oxidation base) | 0.432 | — | — |
| N,N-bis-β-hydroxyethyl-para-phenylenediamine sulfate (oxidation base) | — | 0.78 | — |
| 2-Hydroxyethyl-para-phenylenediamine dihydrochloride (oxidation base) | — | — | 0.675 |
| Common dye support No. | 1 | 2 | 1 |
| Demineralized water qs | 100 g | | 100 g |

Common Dye Support No. 1

| | |
|---|---|
| Oleyl alcohol polyglycerolated with 2 mol of glycerol | 4 g |
| Oleyl alcohol polyglycerolated with 4 mol of glycerol (78% A.M.) | 5.69 g A.M. |
| Oleic acid | 3.0 g |
| Oleylamine containing 2 mol of ethylene oxide, sold under the trade name Ethomeen O12 by the company Akzo | 7 g |
| Diethylaminopropyl laurylaminosuccinamate, sodium salt containing 55% A.M. | 3 g A.M. |
| Oleyl alcohol | 5 g |
| Oleic acid diethanolamide | 12 g |
| Propylene glycol | 3.5 g |
| Ethyl alcohol | 7.0 g |
| Dipropylene glycol | 0.5 g |
| Propylene glycol monomethyl ether | 9 g |
| Sodium metabisulfite as an aqueous solution containing 35% A.M. | 0.455 g A.M. |
| Ammonium acetate | 0.8 g |
| Antioxidant, sequestering agent q.s. | |
| Fragrance, preserving agent q.s. | |
| Monoethanolamine q.s. pH 9.8 | |
| Dyes | x g |
| Demineralized water q.s. | 100 g |

Common Dye Support No. 2

| | |
|---|---|
| Oleyl alcohol polyglycerolated with 2 mol of glycerol | 4 g |
| Oleyl alcohol polyglycerolated with 4 mol of glycerol (78% A.M.) | 5.69 g A.M. |
| Oleic acid | 3.0 g |
| Oleylamine containing 2 mol of ethylene oxide, sold under the trade name Ethomeen O12 by the company Akzo | 7 g |
| Diethylaminopropyl laurylaminosuccinamate, sodium salt containing 55% A.M. | 3 g A.M. |
| Oleyl alcohol | 5 g |
| Oleic acid diethanolamide | 12 g |
| Propylene glycol | 3.5 g |
| Ethyl alcohol | 7.0 g |
| Dipropylene glycol | 0.5 g |
| Propylene glycol monomethyl ether | 9 g |
| Sodium metabisulfite as an aqueous solution containing 35% A.M. | 0.455 g A.M. |
| Ammonium acetate | 0.8 g |
| Antioxidant, sequestering agent q.s. | |
| Fragrance, preserving agent q.s. | |
| Aqueous ammonia containing 20% of $NH_3$ | 10 g |
| Dyes | x g |
| Demineralized water q.s. | 100 g |

Method and Application

The composition obtained is mixed, weight for weight, with 20 volumes of aqueous hydrogen peroxide, the pH of which is adjusted with a precise amount of 85% pure orthophosphoric acid (2.5 g/100 g of aqueous hydrogen peroxide) for examples 1 and 3, and at pH=3 for example 2. The mixture is applied to permanent-waved grey hair containing 90% of white hairs, in a proportion of 28 g per 3 g of hair, for 30 min. The hair is then rinsed, washed with a standard shampoo and dried.

The results are given in the table below:

| EXAMPLE | SHADE OBTAINED |
|---|---|
| 1 | Black |
| 2 | Blue |
| 3 | slightly purplish midnight blue |

What is claimed is:

1. A composition for the oxidation dyeing of keratinous fibers comprising, in a medium which is suitable for dyeing:
   a first coupler chosen from at least one 3,5-diaminopyridine derivative corresponding to the following general formula (I):

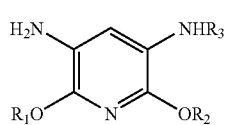

(I)

wherein:
   $R_1$ and $R_2$, which may be identical or different, are chosen from $C_1$–$C_4$ alkyl radicals, $C_1$–$C_4$ monohydroxyalkyl radicals, and $C_2$–$C_4$-polyhydroxyalkyl radicals, $R_3$ is chosen from hydrogen, $C_1$–$C_4$ alkyl radicals, $C_1$–$C_4$ monohydroxyalkyl radicals, $C_2$–$C_4$ polyhydroxyalkyl radicals, and one of their addition salts with an acid;
   a second coupler chosen from at least one meta-phenylenediamine, and one of its addition salts with an acid, wherein the amount of the second coupler ranges from about 0.0001% to about 10% by weight relative to the total weight of the composition; and
   at least one oxidation base chosen from bases of the para-phenylenediamine type, and one of its addition salts with an acid.

2. The composition of claim 1, wherein the keratinous fibers are human keratinous fibers.

3. The composition of claim 2, wherein the human keratinous fibers are human hair.

4. The composition of claim 1, wherein the at least one 3,5-diaminopyridine derivative of formula (I) is chosen from 2,6-dimethoxy-3,5-diaminopyridine, 2,6-diethoxy-3,5-diaminopyridine, 2,6-di(β-hydroxyethyloxy)-3,5-diaminopyridine, and their addition salts with an acid.

5. The composition of claim 1, wherein the at least one 3,5-diaminopyridine derivative of formula (I) is chosen from 2,6-dimethoxy-3,5-diaminopyridine, and one of its addition salts with an acid.

6. The composition of claim 1, wherein the amount of the at least one 3,5-diaminopyridine derivative of formula (I) ranges from about 0.0001% to about 10% by weight relative to the total weight of the composition.

7. The composition of claim 1, wherein the at least one meta-phenylenediamine corresponds to the following formula (II):

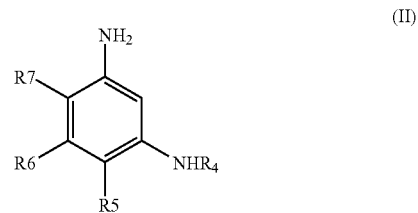

(II)

wherein:
   $R_4$ is chosen from hydrogen, $C_1$–$C_4$ alkyl radicals, $C_1$–$C_4$ monohydroxyalkyl radicals, and $C_2$–$C_4$ polyhydroxyalkyl radicals;
   $R_5$ and $R_6$, which may be identical or different, are chosen from hydrogen, $C_1$–$C_4$ alkyl radicals, and $C_1$–$C_4$ hydroxyalkoxy radicals;
   $R_7$ is chosen from hydrogen, $C_1$–$C_4$ alkoxy radicals, $C_1$–$C_4$ aminoalkoxy radicals, $C_1$–$C_4$ mono-hydroxyalkoxy radicals, $C_2$–$C_4$ polyhydroxyalkoxy radicals, 2,4-diaminophenoxyalkoxy radicals, and their addition salts with an acid.

8. The composition of claim 7, wherein the at least one meta-phenylenediamine of formula (II) is chosen from meta-phenylenediamine, 2,4-diaminophenoxy-ethanol, 2,4-diamino-1-ethoxybenzene, 2-amino-4-N-(β-hydroxyethyl)aminoanisole, 3,5-diamino-1-ethyl-2-methoxybenzene, 3,5-diamino-2-methoxy-1-methylbenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methyl-benzene, 2,4-diamino-5-(β-hydroxyethyloxy)-1-methylbenzene, 2,4-diamino-1-(βγ-dihydroxypropyloxy)-benzene, and 2-amino-4-N-(β-hydroxyethyl)amino-1-methoxybenzene, and their addition salts with an acid.

9. The composition of claim 1, wherein the at least one oxidation base chosen from the para-phenylenediamine type corresponds to the following formula (III):

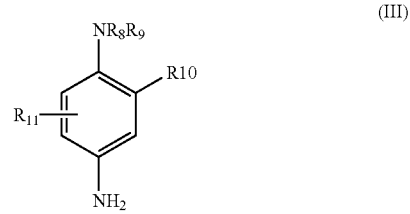

wherein:
- $R_8$ is chosen from hydrogen, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, and $C_1$–$C_4$ alkyl radicals substituted with a group chosen from nitrogenous, phenyl, and 4'-aminophenyl groups;
- $R_9$ is chosen from hydrogen, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, and $C_1$–$C_4$ alkyl radicals substituted with a nitrogenous group;
- $R_{10}$ is chosen from hydrogen, halogens, $C_1$–$C_4$ alkyl radicals, $C_1$–$C_4$ monohydroxyalkyl radicals, $C_1$–$C_4$ hydroxyalkoxy radicals, acetylamino($C_1$–$C_4$)alkoxy radicals, $C_1$–$C_4$ mesylaminoalkoxy radicals, and carbamoylamino($C_1$–$C_4$)alkoxy radicals; and
- $R_{11}$ is chosen from hydrogen, halogens, $C_1$–$C_4$ alkyl radicals, and their addition salts with an acid.

10. The composition of claim 9, wherein the halogens are chosen from chlorine, bromine, iodine, and fluorine.

11. The composition of claim 9, wherein the para-phenylenediamine is chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(βγ-dihydroxypropyl)-para-phenylenediamine, N-(4'-aminophenyl)-para-phenylenediamine, N-phenyl-para-phenylenediamine, N-(β-methoxyethyl)-para-phenylenediamine, and 2-methyl-1-N-(β-hydroxyethyl)-para-phenylenediamine, and their addition salts with an acid.

12. The composition of claim 1, wherein the amount of the para-phenylenediamine ranges from about 0.0005% to about 12% by weight relative to the total weight of the composition.

13. The composition of claim 1, wherein the composition further comprises one or more additional couplers that are different from said at least one 3,5-diaminopyridine derivative of formula (I) and from said meta-phenylenediamines.

14. The composition of claim 13, wherein the additional couplers are chosen from meta-aminophenols, meta-diphenols, heterocyclic couplers, and their addition salts with an acid.

15. The composition of claim 13, wherein the amount of the additional couplers ranges from about 0.0001% to about 10% by weight relative to the total weight of the composition.

16. The composition of claim 14, wherein the amount of the additional couplers ranges from about 0.0001% to about 10% by weight relative to the total weight of the composition.

17. The composition of claim 1, further comprising one or more additional oxidation bases other than the para-phenylenediamines.

18. The composition of claim 17, wherein the additional oxidation bases are chosen from bisphenylalkylenediamines, para-aminophenols, ortho-aminophenols, and heterocyclic bases.

19. The composition of claim 17, wherein the amount of the additional oxidation bases ranges from about 0.0005% to about 12% by weight relative to the total weight of the composition.

20. The composition of claim 18, wherein the amount of the additional oxidation bases ranges from about 0.0005% to about 12% by weight relative to the total weight of the composition.

21. The composition of claim 1, wherein the addition salts with an acid are chosen from hydrochlorides, hydrobromides, sulfates, tartrates, lactates, and acetates.

22. A method for dyeing keratinous fibers comprising applying to the keratinous fibers at least one dye composition for the oxidation dyeing of keratinous fibers comprising, in a medium which is suitable for dyeing:
- a first coupler chosen from at least one 3,5-diaminopyridine derivative corresponding to the following general formula (I):

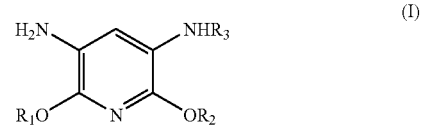

wherein:
- $R_1$ and $R_2$, which may be identical or different, are chosen from $C_1$–$C_4$ alkyl radicals, $C_1$–$C_4$ monohydroxyalkyl radicals, and $C_2$–$C_4$-polyhydroxyalkyl radicals,
- $R_3$ is chosen from hydrogen, $C_1$–$C_4$ alkyl radicals, $C_1$–$C_4$ monohydroxyalkyl radicals, $C_2$–$C_4$ polyhydroxyalkyl radicals, and one of their addition salts with an acid;
- a second coupler chosen from at least one meta-phenylenediamine, and one of its addition salts with an acid, wherein the amount of the second coupler ranges from about 0.0001% to about 10% by weight relative to the total weight of the composition; and
- at least one oxidation base chosen from bases of the para-phenylenediamine type, and one of its addition salts with an acid,
- wherein color is developed by exposing the dye composition to an acidic, neutral, or alkaline pH using an oxidizing agent that is added to the dye composition at the time of use, or that is present in an oxidizing composition applied to the fibers simultaneously or sequentially.

23. The method of claim 22, wherein the keratinous fibers are human keratinous fibers.

24. The method of claim 23, wherein the human keratinous fibers are human hair.

25. The method of claim 22, wherein the oxidizing agent present in the oxidizing composition is chosen from hydrogen peroxide, urea peroxide, alkali metal bromates, persalts, peracids, and enzymes.

26. The method of claim 22, wherein the persalts are chosen from perborates, percarbonates, and persulfates.

27. A multi-compartment device or multi-compartment dyeing kit comprising:
   (1) a first compartment that contains a composition for the oxidation dyeing of keratinous fibers comprising, in a medium which is suitable for dyeing:
   a first coupler chosen from at least one 3,5-diaminopyridine derivative corresponding to the following general formula (I):

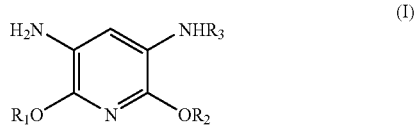

(I)

wherein:
   $R_1$ and $R_2$, which may be identical or different, are chosen from $C_1$–$C_4$ alkyl radicals, $C_1$–$C_4$ monohydroxyalkyl radicals and $C_2$–$C_4$-polyhydroxyalkyl radicals,
   $R_3$ is chosen from hydrogen, $C_1$–$C_4$ alkyl radicals, $C_1$–$C_4$ monohydroxyalkyl radicals, $C_2$–$C_4$ polyhydroxyalkyl radicals, and one of their addition salts with an acid;
   a second coupler chosen from at least one meta-phenylenediamine, and one of its addition salts with an acid, wherein the amount of the second coupler ranges from about 0.0001% to about 10% by weight relative to the total weight of the composition,
   at least one oxidation base chosen from bases of the para-phenylenediamine type, and one of its addition salts with an acid; and
   (2) a second compartment that contains an oxidizing composition.

28. The device of claim 27, wherein the oxidizing composition comprises an oxidizing agent chosen from hydrogen peroxide, urea peroxide, alkali metal bromates, persalts, peracids and enzymes.

29. The device of claim 28, wherein, the persalts are chosen from perborates, percarbonates, and persulfates.

* * * * *

UNITED STATES PATENT AND TRADEMARK OFFICE
CERTIFICATE OF CORRECTION

PATENT NO. : 7,141,079 B2 Page 1 of 2
APPLICATION NO. : 10/257358
DATED : November 28, 2006
INVENTOR(S) : Marie-Pascale Audousset It is certified that error appears in the above-identified patent and that said Letters Patent is hereby corrected as shown below:

On the title page, in item (*), add --This patent is subject to a terminal disclaimer.--.

In claim 8, column 10, line 61, "3,5-diamino-1 -ethyl-2-methoxybenzene," should read --3,5-diamino-l-ethyl-2-methoxybenzene,--.

In claim 8, column 10, line 67 through column 11, line 1, "2,4-diamino-l-(βγ-dihydroxypropyloxy)-benzene," should read --2,4-diamino-1-(β,γ-dihydroxypropyloxy)-benzene,--.

In claim 11, column 11, lines 42-43, "2,6-dimethyl -para-phenylenediamine," should read --2,6-dimethyl-para-phenylenediamine,--.

In claim 11, column 11, lines 43-44, "2,5-dimethyl-para    -phenylenediamine," should read --2,5-dimethyl-para-phenylenediamine,--.

In claim 11, column 11, line 45, "N,N-diethyl-para -phenylenediamine," should read --N,N-diethyl-para-phenylenediamine,--.

In claim 11, column 11, lines 47-48, "N  ,N-bis(β-hydroxyethyl)-para-phenylenediamine," should read --N,N-bis(β-hydroxyethyl)-para-phenylenediamine,--.

In claim 11, column 11, lines 51-52, "2-isopropyl     -para-phenylenediamine," should read --2-isopropyl-para-phenylenediamine,--.

In claim 11, column 11, lines 53-54, "2-hydroxymethyl        -para-phenylenediamine," should read --2-hydroxymethyl-para-phenylenediamine,--.

In claim 11, column 11, lines 55-56, "N,N-(ethyl        -β-hydroxyethyl)-para-phenylenediamine," should read --N,N-(ethyl-β-hydroxyethyl)-para-phenylenediamine,--.

In claim 11, column 11, lines 56-57, "N-(βγ-dihydroxypropyl)-para-phenylenediamine," should read --N-(β,γ-dihydroxypropyl)-para-phenylenediamine,--.

In claim 11, column 11, line 58, "N-phenyl-para -phenylenediamine," should read --N-phenyl-para-phenylenediamine,--.

UNITED STATES PATENT AND TRADEMARK OFFICE
CERTIFICATE OF CORRECTION

PATENT NO. : 7,141,079 B2
APPLICATION NO. : 10/257358
DATED : November 28, 2006
INVENTOR(S) : Marie-Pascale Audousset It is certified that error appears in the above-identified patent and that said Letters Patent is hereby corrected as shown below:

In claim 18, column 12, line 20, "para -aminophenols," should read --para-aminophenols,--.

Signed and Sealed this

Tenth Day of April, 2007

JON W. DUDAS
*Director of the United States Patent and Trademark Office*